(12) United States Patent
Lembcke et al.

(10) Patent No.: US 12,196,637 B2
(45) Date of Patent: Jan. 14, 2025

(54) METHOD, APPARATUS AND COMPUTER PROGRAM FOR MONITORING AIR PRESSURE CHANGE TO REDUCE BAROTRAUMA

(71) Applicant: Cirrus Healthcare Products, L.L.C., Cold Spring Harbor, NY (US)

(72) Inventors: Jeremiah J. Lembcke, Hood River, OR (US); Grant A. O'Connell, Los Angeles, CA (US)

(73) Assignee: CIRRUS HEALTHCARE PRODUCTS, L.L.C., Cold Spring Harbor, NY (US)

( * ) Notice: Subject to any disclaimer, the term of this patent is extended or adjusted under 35 U.S.C. 154(b) by 271 days.

(21) Appl. No.: 17/980,453

(22) Filed: Nov. 3, 2022

(65) Prior Publication Data

US 2023/0142482 A1    May 11, 2023

Related U.S. Application Data

(60) Provisional application No. 63/276,454, filed on Nov. 5, 2021.

(51) Int. Cl.
*G01L 13/00* (2006.01)
*A61F 11/08* (2006.01)

(52) U.S. Cl.
CPC .............. *G01L 13/00* (2013.01); *A61F 11/08* (2013.01)

(58) Field of Classification Search
None
See application file for complete search history.

(56) References Cited

U.S. PATENT DOCUMENTS

| | | |
|---|---|---|
| 4,470,819 A | 9/1984 | Seay et al. |
| 4,631,960 A | 12/1986 | Wogerbauer |

(Continued)

FOREIGN PATENT DOCUMENTS

| | | |
|---|---|---|
| EP | 3115745 | 1/2017 |
| WO | 0175472 | 5/2002 |
| WO | 2009090396 | 7/2009 |

OTHER PUBLICATIONS

Cirrus Healthcare Products, L.L.C., WeatherX (www.weatherx.com) (Feb. 20, 2019).

(Continued)

*Primary Examiner* — Peter J Macchiarolo
*Assistant Examiner* — Jermaine L Jenkins
(74) *Attorney, Agent, or Firm* — Ware, Fressola, Maguire & Barber LLP

(57) ABSTRACT

In accordance the present invention, a method, apparatus and computer program for monitoring air pressure change are provided that may include receiving a user input selecting a pressure monitoring application, receiving a user input initiating monitoring of an ambient air pressure by the pressure monitoring application, determining a first barometric pressure of the ambient air pressure at a first time, determining a second barometric pressure of the ambient air pressure at a second time, wherein the second time is a predetermined time interval from the first time, comparing the first barometric pressure with the second barometric pressure to determine a first absolute rate of change of the ambient air pressure over the predetermined time interval, and providing an indication to employ protective measures when the first absolute rate of change of the ambient air pressure is equal to or a exceeds a threshold rate of change likely to cause barotrauma.

20 Claims, 8 Drawing Sheets

(56) References Cited

U.S. PATENT DOCUMENTS

| | | | |
|---|---|---|---|
| 5,178,010 | A | 1/1993 | Holzel |
| 5,755,234 | A | 5/1998 | Mobley et al. |
| 5,819,745 | A | 10/1998 | Mobley et al. |
| 6,443,913 | B1 | 9/2002 | Kania |
| 6,741,174 | B2 | 5/2004 | Rhoades et al. |
| 8,171,788 | B2 * | 5/2012 | Ahlstrom ................ G01L 19/08 73/384 |
| 9,571,913 | B2 | 2/2017 | Masaki et al. |
| 9,814,278 | B2 | 11/2017 | Chung et al. |
| 10,064,758 | B2 | 9/2018 | O'Connell et al. |
| 10,667,047 | B2 | 5/2020 | Asada et al. |
| 10,911,089 | B2 | 2/2021 | Jacobsen |
| 10,964,190 | B2 | 3/2021 | Peyrard |
| 11,043,980 | B2 | 6/2021 | Gong et al. |
| 2002/0069883 | A1 | 6/2002 | Hirchenbain |
| 2007/0112279 | A1 | 5/2007 | Iseberg et al. |
| 2009/0270689 | A1 | 10/2009 | Galland |
| 2014/0140567 | A1 | 5/2014 | Leboeuf et al. |
| 2014/0213308 | A1 | 7/2014 | Matthes et al. |
| 2018/0125717 | A1 | 5/2018 | Lawrence |
| 2018/0140233 | A1 | 5/2018 | Lacirignola et al. |
| 2018/0220905 | A1 | 8/2018 | Leboeuf et al. |
| 2018/0325739 | A1 | 11/2018 | O'Connell et al. |
| 2020/0051542 | A1 | 2/2020 | Yamkovoy |
| 2020/0121544 | A1 | 4/2020 | George et al. |
| 2020/0284646 | A1 | 9/2020 | Goldstein et al. |

OTHER PUBLICATIONS

ForeFlight, LLC, ForeFlight 7: Cabin Altitude Advisor in the Settings menu. (Apr. 27, 2015).

International Search Report for International Application No. PCT/US2022/048880, mailed Feb. 16, 2023, 2 pages.

* cited by examiner

METHOD, APPARATUS AND COMPUTER PROGRAM FOR MONITORING AIR PRESSURE CHANGE TO REDUCE BAROTRAUMA

CROSS-REFERENCE TO RELATED APPLICATIONS

This application claims priority to U.S. Provisional Appl. No. 63/276,454 filed Nov. 5, 2021, which is hereby incorporated by reference in its entirety.

BACKGROUND OF THE INVENTION

1. Field of the Invention

The present invention relates to exemplary embodiments of a method, apparatus and computer program for monitoring air pressure change in order to reduce barotrauma. More particularly, the present invention is directed to a method, apparatus and computer program configured to monitor and log ambient air pressure to identify air pressure changes that may result in barotrauma and inform a user when to initiate protective measures to alleviate or eliminate such barotrauma, and also inform the user when such protective measures may no longer be needed.

2. Description of Related Art

The middle ear is an air-filled cavity connected to the outside environment via the Eustachian tube. Under normal conditions, there is no difference between the air pressure in the outside environment and the middle ear. This condition is illustrated in FIG. 1, which is a schematic drawing of the ear, and shows under normal conditions there is no pressure difference across the eardrum, i.e., between the outside environment and the middle ear. However, when there is a change in air pressure, such as when there is a change in barometric pressure due to weather conditions, change in elevation, take-off or landing in an aircraft, etc., there is a difference in the air pressure between the middle ear and the outside environment. Under conditions in which such a pressure differential exists, the Eustachian tube acts as a valve between the outside environment and the middle ear. In this capacity, the Eustachian tube opens for a fraction of a second in response to swallowing or yawning, allowing airflow through the Eustachian tube so the pressure differential between the outside environment and the middle ear equilibrate.

During a decrease in barometric pressure, for example during take-off in an aircraft, the air pressure in the outside environment, that is, the environment outside the middle ear, can become less than that of the pressure inside the middle ear. Under these conditions, the positive relative pressure in the middle ear forces air out of the Eustachian tube thereby lowering the pressure inside the middle ear to the same pressure as the outside environment. In other words, the air travels from a relative high pressure environment of the middle ear through the Eustachian tube to a relative lower pressure environment of the outside environment to equilibrate pressure between the middle ear and the outside environment. If the Eustachian tube is blocked or does not open as normal, as described more fully below, the positive pressure in the middle ear applies pressure to the ear drum, as shown schematically in FIG. 2, causing it to bow outward toward the external ear cavity. This bowing of the ear drum can cause discomfort and potential barotrauma as a result of the difference in pressure between the middle ear and external ear cavity.

Conversely, during an increase in barometric pressure, the air pressure of the outside environment is greater than that of the pressure inside the middle ear. Under these conditions, the negative relative pressure in the middle ear causes airflow from the outside environment through the Eustachian tube and into the middle ear, thereby increasing the pressure inside the middle ear to the same pressure as the outside environment. Again, under conditions in which the Eustachian tube is blocked or does not open as normal, the negative pressure in the middle ear causes deformation of the ear drum, bowing it inward toward the middle ear, as shown schematically in FIG. 7. This bowing of the ear drum can cause discomfort and potential barotrauma as a result of the difference in pressure between the middle ear and external ear cavity.

Under normal circumstances, when there is no or little blockage and proper functioning of the Eustachian tube, as the pressure differential increases across the ear drum between the middle ear and outside environment, voluntary swallowing and/or chewing can cause equilibration of the pressure as a result of passage of air through the Eustachian tube when opened. Prior devices, such as the earplugs discussed in U.S. Pat. No. 5,467,784, which is hereby incorporated by reference in its entirety, provide for pressure regulation of the ear canal during rapid changes in pressure associated with commercial air travel, for example during take-off and landing. During take-off, commercial aircraft cabins begin to pressurize to an eventual cruising pressure equivalent to what the barometric pressure would be at approximately 8,000 feet, and the opposite is true upon landing. During take-off and landing the pressure can become variable as the ambient pressure within the aircraft is being adjusted to the desired air pressure. This variation in pressure can cause discomfort, for example ear pain, and potential barotrauma, i.e., damage as a result of a pressure differential, for the reasons discussed above with respect to FIGS. 2 and 7. While prior devices, such as the earplugs discussed in U.S. Pat. No. 5,467,784, may alleviate the discomfort or potential barotrauma, such devices must be inserted and worn during times when the pressure changes are likely to cause discomfort and/or barotrauma. It is possible a user may only have an educated guess as to when the devices should be inserted and removed, resulting in the user inserting or removing the devices at inopportune times, or the user may forget to insert the devices all together.

Therefore, what is needed is a means for informing a user of devices configured to reduce ear discomfort and/or the potential for barotrauma, such as the earplugs discussed in U.S. Pat. No. 5,467,784, when such devices should be inserted and removed during travel in an aircraft or other vehicle where the user may experience rapid and/or variable changes in barometric pressure leading to ear discomfort or barotrauma, for example in a train or other land vehicle, such as a car or bus, ascending or descending a mountain.

SUMMARY OF THE INVENTION

The present invention contemplates the provision of a method, apparatus and computer program for providing ambient pressure data to assist in the timing of a remedy to ameliorate involuntary physical distress caused by a rapid change in the ambient pressure during air travel or other travel events that could have pressure changes. The remedy according to an exemplary embodiment of the present invention may be an earplug including a body having a first end, a second end and a longitudinal axis extending from the first end to the second end, a bore defined within the body and extending from the first end to the second end along the longitudinal axis of the body, and a pressure regulator positioned within the bore and providing regulated air flow through the earplug.

It is an object of the present invention to provide a computer program designed to capture real time barometric pressure data from a pressure sensor integrated into cellular telephone hardware.

It is further an object of the present invention to provide a computer program utilizing the captured information to generate visible data for the users to interact with the data collected.

It is still another object of the present invention to provide a computer program configured to inform the user when pressure has stabilized allowing for the removal of the earplugs.

It is yet another object of the present invention to provide a computer program having a notification on when a change in pressure is detected and configured to notify the user if the pressure change is unexpected.

It is a further object of the present invention to provide a computer program configured to save pressure data for review, allowing for future improvements in the proper use of the earplugs for specific flights or other travel events.

It is still another object of the present invention to provide an application configured to use a barometer present in a mobile device, such as a cellular telephone, to provide real time plotting of cabin pressure readings during travel in a vehicle, such as an aircraft, train, bus, truck or car.

It is yet another object of the present invention to provide an application configured to take barometric pressure readings at a predetermined interval, such as once per second, and plot the readings in a graph for display to the user.

It is yet another object of the present invention to provide an application configured to provide the user with a notification that the earplugs can be removed when pressure has reached a non-variable and/or stable level.

It is an object of this invention to provide an application configured to provide the user with a notification to reinsert the earplugs when pressure becomes variable and/or unstable after reaching a non-variable and/or stable level.

It is a further object of this invention to provide an application configured to log the detected pressure data and/or prepare a summary of the pressure data so the data and/or summary can be accessed by the user.

It is yet another object of the present invention to provide an application configured to label a pressure graph of recorded pressure changes with colors, for example, greens, yellows, reds, based on the likelihood of a recorded pressure change causing discomfort and/or barotrauma in order to provide a visual element to an unseen force that can cause discomfort and/or barotrauma.

It is still another object of the present invention to provide an application configured to instruct a user when to insert and remove earplugs designed to reduce or eliminate discomfort and/or barotrauma associated with rapid barometric pressure changes.

It is yet another object of the present invention to provide an application configured to collect and log real time data of a user's experience during in flight cabin pressure changes.

It is a further object of the present invention to provide an application configured to educate a user about in flight pressure changes, and illustrate the benefits and functionality of earplugs designed to reduce or eliminate discomfort and/or barotrauma associated with rapid barometric pressure changes.

It is still another object of the present invention to provide an application configured to provide real time barometric pressure plotting along a graph.

It is yet another object of the present invention to provide an application configured to initiate recording of barometric pressure and store the barometric pressure readings during the course of the recording.

It is a further object of the present invention to provide an application configured to provide a push notification when the pressure becomes steady or drops at a predetermined rate so the user has guidance when to inset or remove earplugs designed to reduce or eliminate discomfort and/or barotrauma associated with rapid barometric pressure changes.

It is yet another object of the present invention to provide an application having a summary of past recorded flight barometric pressure data for access and review by the user.

In accordance with an exemplary aspect of the present invention, a method for monitoring air pressure change is provided that may include receiving a user input selecting a pressure monitoring application, receiving a user input initiating monitoring of an ambient air pressure by the pressure monitoring application, determining a first barometric pressure of the ambient air pressure at a first time, determining a second barometric pressure of the ambient air pressure at a second time, the second time being a predetermined time interval from the first time, comparing the first barometric pressure with the second barometric pressure to determine a first absolute rate of change of the ambient air pressure over the predetermined time interval, and providing an indication to employ protective measures when the first absolute rate of change of the ambient air pressure is equal to or a exceeds a threshold rate of change likely to cause barotrauma.

In accordance with this exemplary aspect and other exemplary aspects of the present invention, the method may also include determining a third barometric pressure of the ambient air pressure at a third time, the third time being the predetermined time interval from the second time, comparing the second barometric pressure with the third barometric pressure to determine a second absolute rate of change of the ambient air pressure over the predetermined time interval, continuing to provide the indication to employ protective measures when the second absolute rate of change of the ambient air pressure over the predetermined time interval is equal to or exceeds the threshold rate of change likely to cause barotrauma, and providing an indication to discontinue protective measures when the second absolute rate of change of the ambient air pressure over the predetermined time interval is less than the threshold rate of change likely to cause barotrauma.

In accordance with this exemplary aspect and other exemplary aspects of the present invention, the protective measures may include a pair of earplugs each having a pressure regulator with an air leakage rate of $6.1 \times 10^{-5}$ to $1.4 \times 10^{-3}$ cc/sec, and the method may also include inserting the earplugs into ear canals of a user.

In accordance with this exemplary aspect and other exemplary aspects of the present invention, the method may also include setting the threshold rate of change to at least 3 mbar/sec.

In accordance with this exemplary aspect and other exemplary aspects of the present invention, the method may also include determining a fourth barometric pressure of the ambient air pressure at a fourth time, wherein the fourth time is the predetermined time interval from the third time, and comparing the third barometric pressure with the fourth barometric pressure to determine a third absolute rate of change of the ambient air pressure over the predetermined time interval.

In accordance with this exemplary aspect and other exemplary aspects of the present invention, the method may also include organizing at least the first barometric pressure, the second barometric pressure and the third barometric pressure for presentation as a graph of measured ambient air pressure over time.

In accordance with this exemplary aspect and other exemplary aspects of the present invention, the method may also include storing at least the first barometric pressure and the second barometric pressure for retrieval at a later time.

In accordance with an exemplary aspect of the present invention, an apparatus comprising at least one processor and at least one memory including an application that is executable by the at least one processor to cause the apparatus at least to carry out a method for monitoring air pressure change including receiving a user input selecting a pressure monitoring application, receiving a user input initiating monitoring of an ambient air pressure by the pressure monitoring application, determining a first barometric pressure of the ambient air pressure at a first time, determining a second barometric pressure of the ambient air pressure at a second time, the second time being a predetermined time interval from the first time, comparing the first barometric pressure with the second barometric pressure to determine a first absolute rate of change of the ambient air pressure over the predetermined time interval, and providing an indication to employ protective measures when the first absolute rate of change of the ambient air pressure is equal to or a exceeds a threshold rate of change likely to cause barotrauma.

In accordance with this exemplary aspect and other exemplary aspects of the present invention, the application is executable by the at least one processor to further cause the apparatus to carry out determining a third barometric pressure of the ambient air pressure at a third time, the third time being the predetermined time interval from the second time, comparing the second barometric pressure with the third barometric pressure to determine a second absolute rate of change of the ambient air pressure over the predetermined time interval, continuing to provide the indication to employ protective measures when the second absolute rate of change of the ambient air pressure over the predetermined time interval is equal to or exceeds the threshold rate of change likely to cause barotrauma, and providing an indication to discontinue protective measures when the second absolute rate of change of the ambient air pressure over the predetermined time interval is less than the threshold rate of change likely to cause barotrauma.

In accordance with this exemplary aspect and other exemplary aspects of the present invention, the protective measures comprise a pair of earplugs each having a pressure regulator with an air leakage rate of $6.1 \times 10^{-5}$ to $1.4 \times 10^{-3}$ cc/sec, and employing the protective measures comprises inserting the earplugs into ear canals of a user.

In accordance with this exemplary aspect and other exemplary aspects of the present invention, the threshold rate of change is at least 3 mbar/sec.

In accordance with this exemplary aspect and other exemplary aspects of the present invention, the application is executable by the at least one processor to further cause the apparatus to carry out determining a fourth barometric pressure of the ambient air pressure at a fourth time, wherein the fourth time is the predetermined time interval from the third time, and comparing the third barometric pressure with the fourth barometric pressure to determine a third absolute rate of change of the ambient air pressure over the predetermined time interval.

In accordance with this exemplary aspect and other exemplary aspects of the present invention, the application is executable by the at least one processor to further cause the apparatus to carry out organizing at least the first barometric pressure, the second barometric pressure and the third barometric pressure for presentation as a graph of measured ambient air pressure over time.

In accordance with this exemplary aspect and other exemplary aspects of the present invention, the application is executable by the at least one processor to further cause the apparatus to carry out storing at least the first barometric pressure and the second barometric pressure for retrieval at a later time.

In accordance with an exemplary aspect of the present invention, a nontransitory computer readable medium having a computer program stored thereon that is executable by a processor for causing a portable electronic display device to carry out the method for monitoring air pressure change that includes receiving a user input selecting a pressure monitoring application, receiving a user input initiating monitoring of an ambient air pressure by the pressure monitoring application, determining a first barometric pressure of the ambient air pressure at a first time, determining a second barometric pressure of the ambient air pressure at a second time, the second time being a predetermined time interval from the first time, comparing the first barometric pressure with the second barometric pressure to determine a first absolute rate of change of the ambient air pressure over the predetermined time interval, and providing an indication to employ protective measures when the first absolute rate of change of the ambient air pressure is equal to or a exceeds a threshold rate of change likely to cause barotrauma.

In accordance with this exemplary aspect and other exemplary aspects of the present invention, the nontransitory computer readable medium having the computer program stored thereon is executable by the processor for causing the portable electronic display device to further carry out determining a third barometric pressure of the ambient air pressure at a third time, the third time being the predetermined time interval from the second time, comparing the second barometric pressure with the third barometric pressure to determine a second absolute rate of change of the ambient air pressure over the predetermined time interval, continuing to provide the indication to employ protective measures when the second absolute rate of change of the ambient air pressure over the predetermined time interval is equal to or exceeds the threshold rate of change likely to cause barotrauma, and providing an indication to discontinue protective measures when the second absolute rate of change of the ambient air pressure over the predetermined time interval is less than the threshold rate of change likely to cause barotrauma.

In accordance with this exemplary aspect and other exemplary aspects of the present invention, the protective measures comprise a pair of earplugs each having a pressure regulator with an air leakage rate of $6.1 \times 10^{-5}$ to $1.4 \times 10^{-3}$ cc/sec, and employing the protective measures comprises inserting the earplugs into ear canals of a user.

In accordance with this exemplary aspect and other exemplary aspects of the present, the threshold rate of change is at least 3 mbar/sec.

In accordance with this exemplary aspect and other exemplary aspects of the present invention, the nontransitory computer readable medium having the computer program stored thereon is executable by the processor for causing the portable electronic display device to further carry out determining a fourth barometric pressure of the ambient air pressure at a fourth time, the fourth time being the predetermined time interval from the third time, and comparing the third barometric pressure with the fourth barometric pressure to determine a third absolute rate of change of the ambient air pressure over the predetermined time interval.

In accordance with this exemplary aspect and other exemplary aspects of the present invention, the nontransitory computer readable medium having the computer program stored thereon is executable by the processor for causing the portable electronic display device to further carry out organizing at least the first barometric pressure, the second barometric pressure and the third barometric pressure for presentation as a graph of measured ambient air pressure over time.

In accordance with this exemplary aspect and other exemplary aspects of the present invention, the nontransitory computer readable medium having the computer program stored thereon is executable by the processor for causing the portable electronic display device to further carry out storing at least the first barometric pressure and the second barometric pressure for retrieval at a later time.

BRIEF DESCRIPTION OF THE SEVERAL VIEWS OF THE DRAWINGS

For a fuller understanding of the nature and object of the present invention, reference should be had to the following detailed description taken in connection with the accompanying drawings, in which.

DETAILED DESCRIPTION OF THE INVENTION

The present invention now will be described more fully hereinafter with reference to the accompanying figures, in which exemplary embodiments of the invention are shown. The invention may, however, be embodied in many different forms and should not be construed as limited to the embodiments set forth herein.

Figure 3:
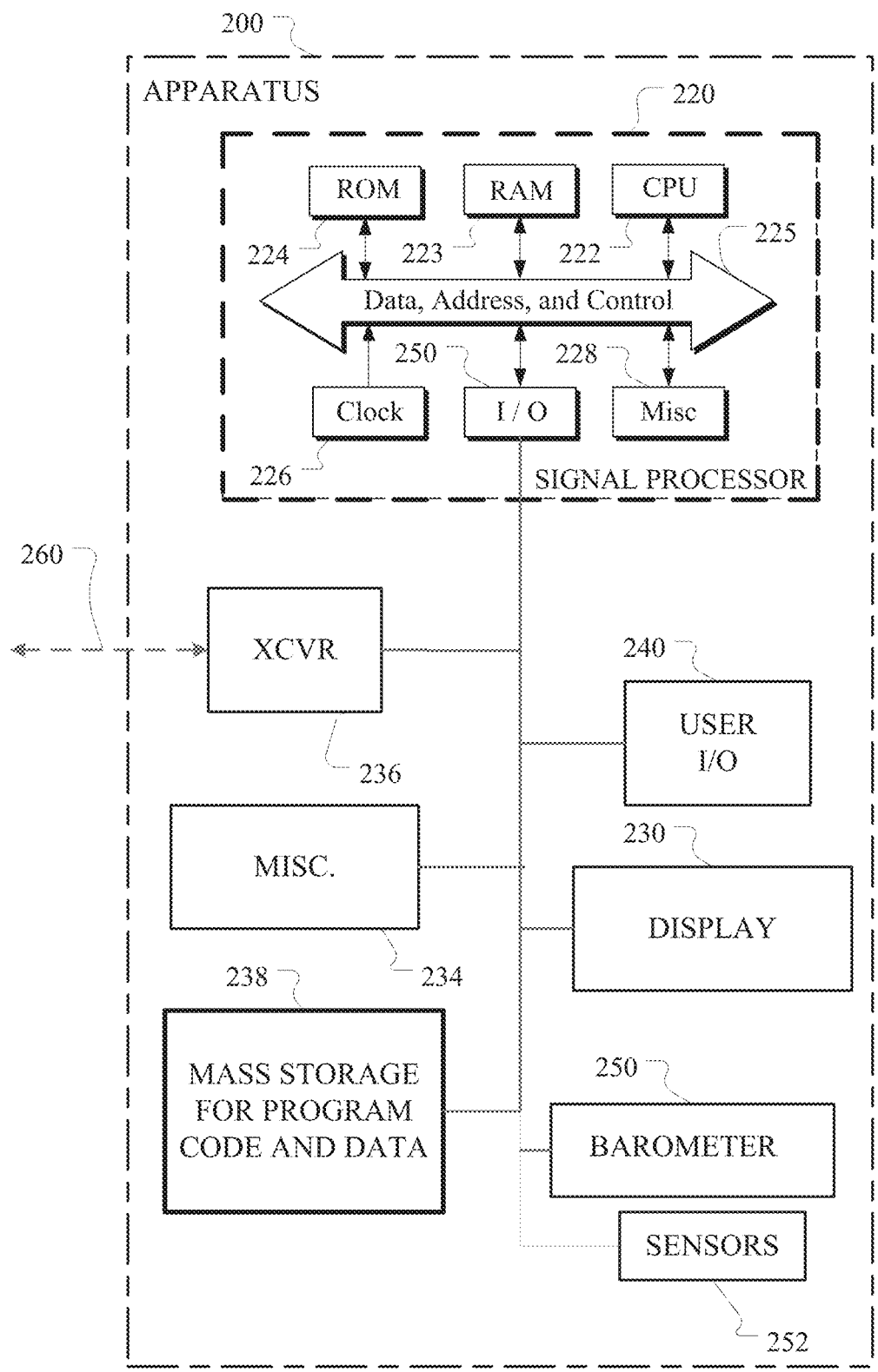
FIG. 3 shows an embodiment of a wireless communication device according to the teachings hereof.

FIG. 3 shows an embodiment of an apparatus 200 in the form of a wireless communication device configured for use with the various aspects of the present invention. An exemplary wireless communication device 200 will be described in more detail with reference to FIG. 3, which illustrates a schematic view of the communication device 200. The communication device 200 is often referred to as user equipment (UE) or terminal, but it is understood these terms are merely exemplary and not limiting as to the nature, function, construction and/or capabilities of the communication device 200. The communication device 200 in accordance with various aspects of the present invention may be any device capable of sending and receiving wireless signals. Non-limiting examples of the communication device 200 may include a mobile station (MS) or mobile device such as a mobile phone or what is known as a "smart phone", a computer provided with a wireless interface card or other wireless interface facility (e.g., USB dongle), personal data assistant (PDA) or a tablet provided with wireless communication capabilities, or any combinations of these or the like. The communication device 200 may be for example a mobile device, that is, a device not fixed to a particular location, or it may be a stationary device. The communication device 200 may need human interaction for communication, or may not need human interaction for communication. The communication device 200 may provide, for example, communication of data for carrying communications such as voice, electronic mail (email), text message, multimedia and the like. Users may thus be offered and provided numerous services via their communication devices 200. Non-limiting examples of these services comprise two-way or multi-way calls, data communication or multimedia services or simply an access to a data communications network system, such as the Internet. Users may also be provided broadcast or multicast data. Non-limiting examples of the content comprise downloads, television and radio programs, videos, advertisements, various alerts and other information.

The wireless communication device 200 may include at least one signal processor 220 that includes at least one central processing unit (CPU) 222 and at least one memory device 224 including computer program code configured to, with the at least one central processing unit 222, cause the communication device 200 at least to carry out certain steps. The wireless communication device 200 may include a user input interface arrangement such as shown as a user input/output device 240 that is responsive to receiving a user input. Such a user input might be made by a finger or stylus touching a touch sensitive screen surface (touchscreen) of a display 230. Thus, as shown in a step 168 in FIG. 1B, the user input device 240 of the exemplary wireless communication device 200 of FIG. 3 may receive and condition the sensed touch input and send a signal to the signal processor 220 that includes the above mentioned at least one CPU 222 and the at least one memory device 224. The received touch input from the user in step 168 may be a selection of a pressure monitoring application displayed as an icon on the screen of the display 230 of the exemplary wireless communication device 200. When the wireless communication device 200 is held in the hand or hands of the user, the screen of the display 230 is visible to the user and pressure monitoring application imagery may be presented via the pressure monitoring application so as to be viewable by the user. In response to the user input in step 168 of FIG. 1B, a pressure monitoring application launch signal may be generated by the signal processor 220. If the pressure monitoring application is stored on the Read Only Memory (ROM) 224, the pressure monitoring application launch signal may be used internally within the signal processor 220 to launch the pressure monitoring application. Or, it could be transmitted to a memory device 238 that may have the executable code for the pressure monitoring application stored in whole or in part therein. The launch of the pressure monitoring application causes the pressure monitoring application to be presented on the display 230. In an embodiment, it may then prompt the user to input other information concerning the functionality and operation of the pressure monitoring application, for example the predetermined intervals of reading, monitoring, recording and/or communicating the ambient barometric pressure of the wireless communication device 200.

Figure 1B:
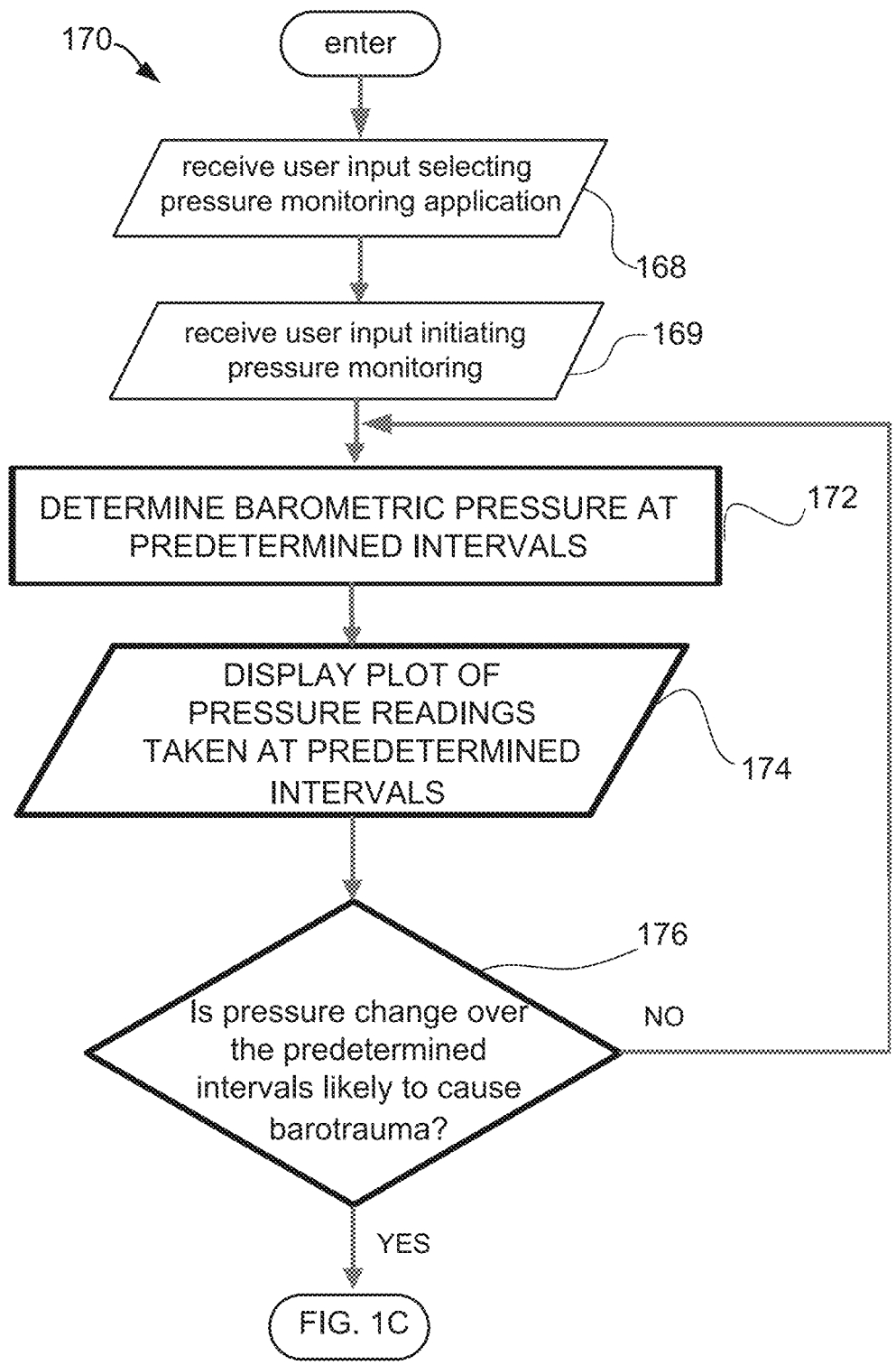
FIGS. 1B and 1C are an exemplary flowchart that shows the wireless communication device of FIG. 3 in operation during running of an exemplary pressure monitoring application according to the teachings hereof.

In operation, as shown by a step 169 in FIG. 1B, the wireless communication device 200 receives user input initiating pressure monitoring by the pressure monitoring application. For example, the user may be present in a situation, such as during a commercial aircraft flight, where monitoring of air pressure is desired. A step 172 may then be performed to determine the barometric pressure at the location of the wireless communication device 200, for instance using the barometer 250 of the wireless communication device 200. The barometer 250 may be responsive to signals originating from the pressure monitoring application, and configured to transmit the barometric pressure in the ambient environment of the wireless communication device 200 at predetermined intervals, for example every second, every minute or any other predetermined amount of time, to the pressure monitoring application for logging and/or display of the barometric pressures. The barometer 250 by itself or the barometer 250 in conjunction with the signal processor 220 is able to determine the predetermined interval for reading the barometric pressure and communicating such barometric pressure to the pressure monitoring application.

As shown in a step 174, the pressure monitoring application is configured to display a plot of pressure readings taken at each of the predetermined intervals on the display 230 of the wireless communication device 200. In step 176, the pressure monitoring application is configured to continuously calculate the likelihood of barotrauma due to the barometric pressure readings provided from the barometer 250 and recorded by the pressure monitoring application. The pressure monitoring application is configured to determine whether the recorded pressure changes are rapid enough to cause the user discomfort and/or barotrauma or likely to lead to user discomfort and/or barotrauma. If a pressure change or expected pressure change based on a trend of one or more pressure changes is determined to be rapid enough to cause discomfort and/or barotrauma, the pressure monitoring application sends a notification in step 178 of FIG. 1C for the user to employ protective measures, such as inserting earplugs designed to reduce or eliminate discomfort and/or barotrauma associated with rapid barometric pressure changes. The notification can be in the form of a graphic or other image on the display 230 of the wireless communication device 200 and/or an audible notification or other visual indication such as a blinking light on the wireless communication device 200. If the pressure changes are determined to not be rapid enough to cause discomfort and/or barotrauma, then the process returns to step 172 and continues to determine the barometric pressure at predetermined intervals, for example every second. Once step 178 has been initiated, the pressure monitoring application continues to determine the barometric pressure at predetermined intervals in a step 180. The pressure monitoring application will continue to log barometric pressure readings, and in step 182 determine whether the pressure change over the predetermined intervals, either based on change between each interval or over a set number of intervals, are likely to cause discomfort and/or barotrauma. If the answer to step 182 is in the affirmative, then the pressure monitoring application may either continue to provide an indication for the user to employ protective measures as in step 178 or simply refrain from providing the user any further indications since the previous indication to employ protective measures still applies. This may be a user selected option, for example whether to continue to send indications or only send a single indication as to whether protective measures are needed. This could also be an indication in the form of color coding on a graph of the pressure monitoring application displayed on the display 230, for example, providing a certain color such as red on the graph when protective measures should remain employed. If the pressure change is determined in step 182 to be unlikely to cause discomfort and/or barotrauma, then in step 184 the pressure monitoring application provides an indication to the user to discontinue the protective measures, for example by removing the previously inserted earplugs. In step 186, if the user discontinues pressure monitoring, the pressure monitoring application ends and no longer requests the current barometric pressures from the barometer 250 of the wireless communication device 200. In step 186 if the user does not discontinue pressure monitoring, the pressure monitoring application returns to step 180 and continues to determine the barometric pressure at predetermined intervals. In this manner, the pressure monitoring application will continue to either provide an indication to the user to employ protective measures in step 178 or discontinue protective measures in step 184 depending upon the variability of the barometric pressure recorded by the barometer 250 of the wireless communication device 200. A nontransitory computer readable medium such as the ROM 224 or the mass storage device 238 may have a computer program stored thereon that is executable by the signal processor 220 for causing the wireless communication device 200 to carry out a method such as shown FIGS. 1B and 1C by the pressure monitoring application.

Figure 1C:
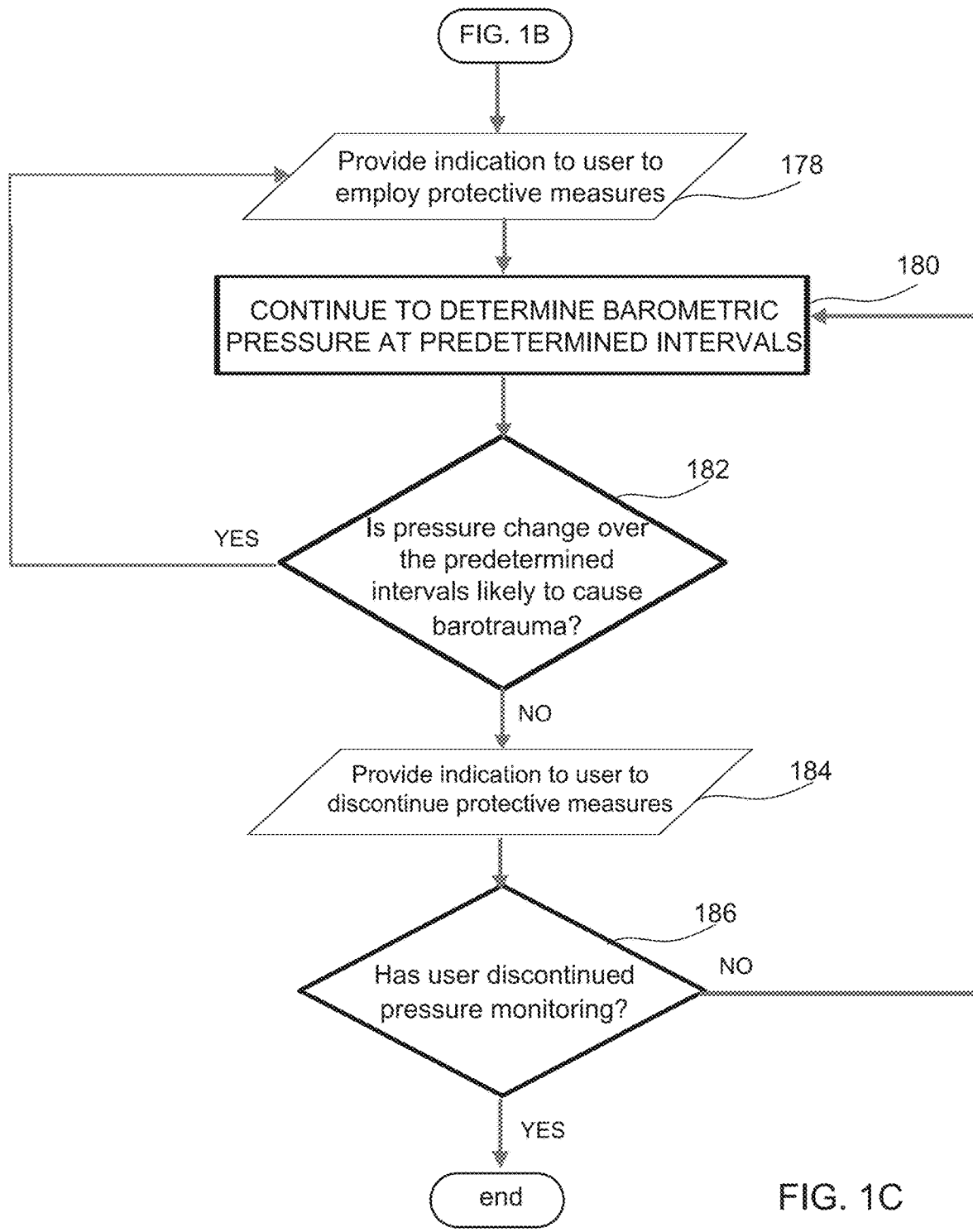

Thus the wireless communication device 200 may be understood as a product including at least one processor 220 and at least one memory 224, 223, 238 including an application that is executable by the at least one processor to cause the wireless communication device 200 at least to carry out a method such as shown in FIGS. 1B and 1C.

Figure 1:
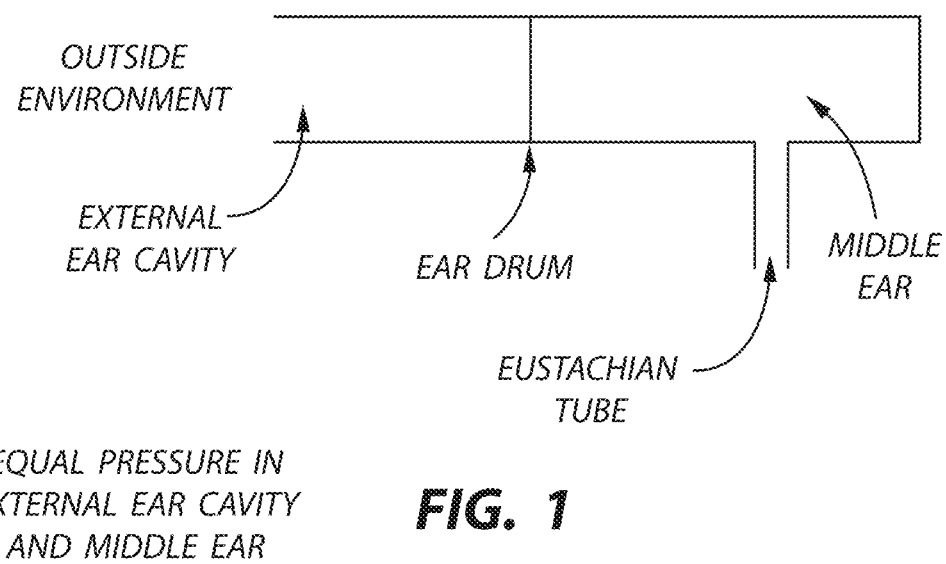
FIG. 1 is a schematic view of an ear in which there is no pressure differential between the external outside environment and the middle ear.
Figure 2:
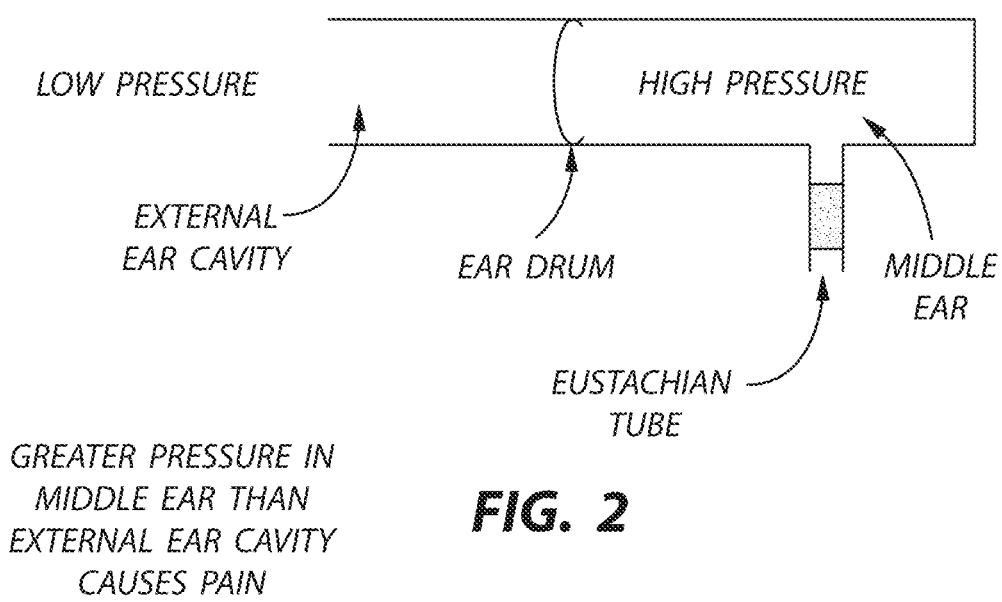
FIG. 2 is a schematic view of an ear in which there is a pressure differential between the external outside environment and the middle ear wherein the pressure in the middle ear is greater than the pressure in the external environment, and wherein the Eustachian tube is at least partially blocked or not functioning normally.
Figure 9:
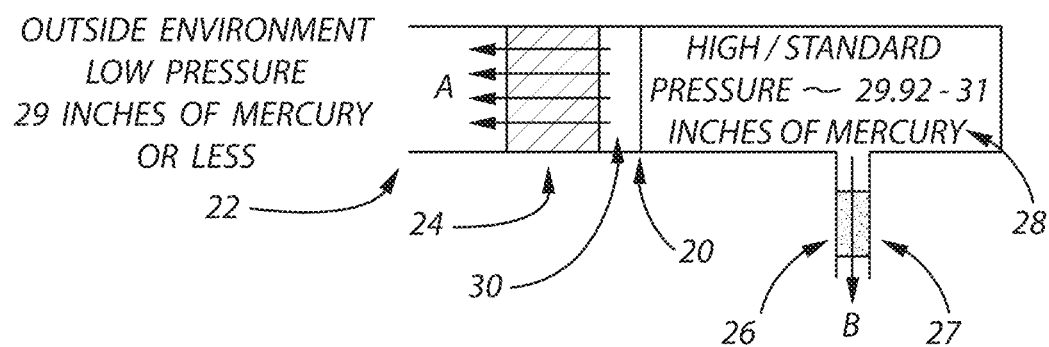
FIG. 9 is a schematic view of an ear in which an exemplary earplug configured for use with the present invention is disposed, and in which there is a pressure differential between the external outside environment and the middle ear, the pressure being greater in the middle ear than in the exterior environment, illustrating a change in barometric pressure, and wherein the Eustachian tube is blocked or not functioning normally.
Figure 10:
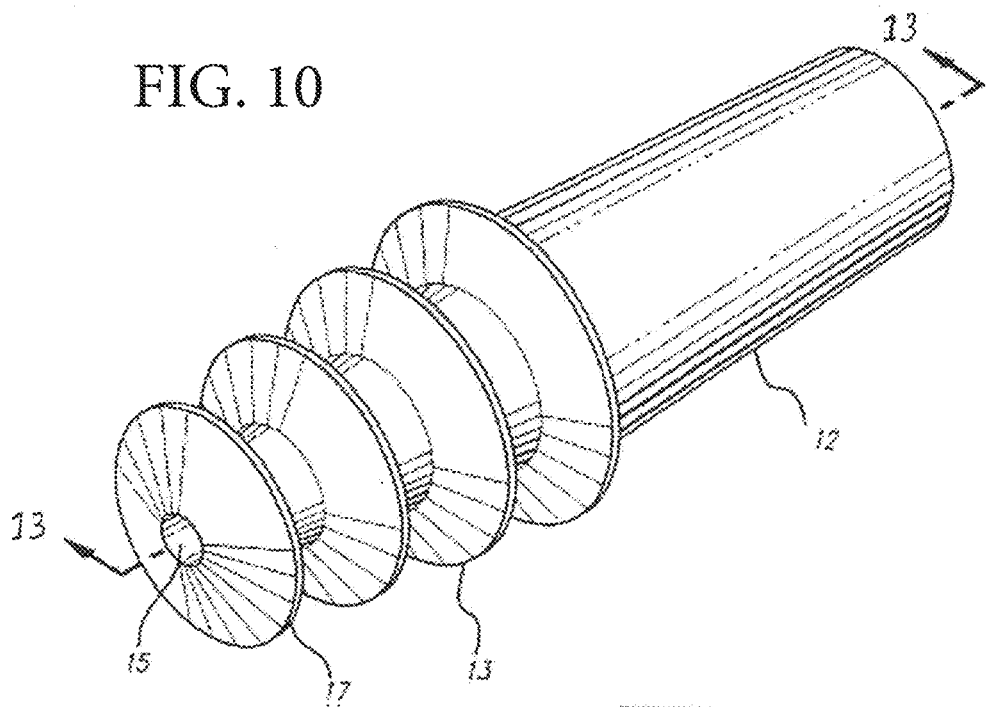
FIG. 10 is a perspective view of an exemplary embodiment of the earplug configured for use with the present invention.
Figure 11:
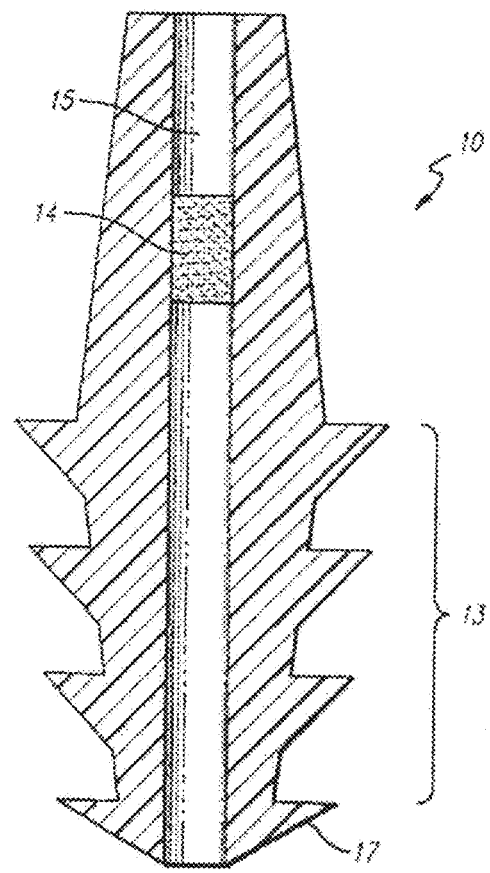
FIG. 11 is a cross-sectional view of the exemplary embodiment of the earplug taken through line 13-13 of FIG. 10.

In accordance with an exemplary embodiment of the present invention, the protective measures may be earplugs designed to reduce or eliminate discomfort and/or barotrauma associated with rapid barometric pressure changes and/or variations. The earplugs may be those disclosed in U.S. Pat. No. 5,467,784, which has been incorporated by reference in its entirety, but for the purposes readability portions will be specifically discussed herein. An exemplary embodiment of an earplug configured for use with the present invention is illustrated in FIGS. 10 and 11. FIG. 9 is a schematic illustration of the operation of the earplugs configured for use with the present invention under conditions comparable to those of FIG. 2, except for the use of the exemplary embodiment of the earplug according to the present invention. More specifically, FIG. 9 depicts the effect of a decrease in barometric pressure. The decrease may be significant and/or rapid enough to cause ear discomfort and/or barotrauma, for example as a result of a blockage of the Eustachian tube 26 or because the Eustachian tube 26 has not had sufficient time to open and equilibrate the pressure between the outside environment and middle ear 28. In FIG. 9, the outside environment has a lower barometric pressure, for example 29 inches of mercury or lower (14.243 psi or less; 982.05 mbar or less), than the pressure inside the middle ear 28, which is still at the barometric pressure, for example 29.92 to 31 inches of mercury (14.695 to 15.225 psi; 1,013.25 to 1,049.78 mbar), before the decrease of barometric pressure. The pressure inside the middle ear is a result of the middle ear being pressurized and filled with air prior to the decrease in barometric pressure, and not being able to equilibrate to the current ambient pressure because the Eustachian tube 26 is blocked, schematically depicted at 27, or fails to functional normally or rapid enough so that the air in the middle ear 28 cannot escape through the Eustachian tube 26, or at least not at the desired rate sufficient to cause the desired depressurization of the middle ear 28 so as to equilibrate the pressure inside the middle ear 28 with the outside environment.

However, because of the installation of the earplug 24, which is schematically depicted in FIG. 9, the pressure in the volume between the ear drum 20 and the earplug 24 remains at the prior barometric pressure before the decrease in barometric pressure, and this prior barometric pressure is the same as the pressure in the middle ear 28 or at a sufficiently close pressure so as to not cause noticeable ear discomfort or barotrauma. The earplug 24 is adapted to slowly release air in the volume 30 to the outside environment through the external ear canal 22, and as shown, airflow in direction A illustrated by the arrows occurs. Similarly, provided that there is only partial blockage of the Eustachian tubes, airflow through the blockage 27 travels in the direction depicted by arrow B, so that the pressure in the middle ear equilibrates with the current ambient barometric pressure as it exists in the outside environment.

Figure 7:
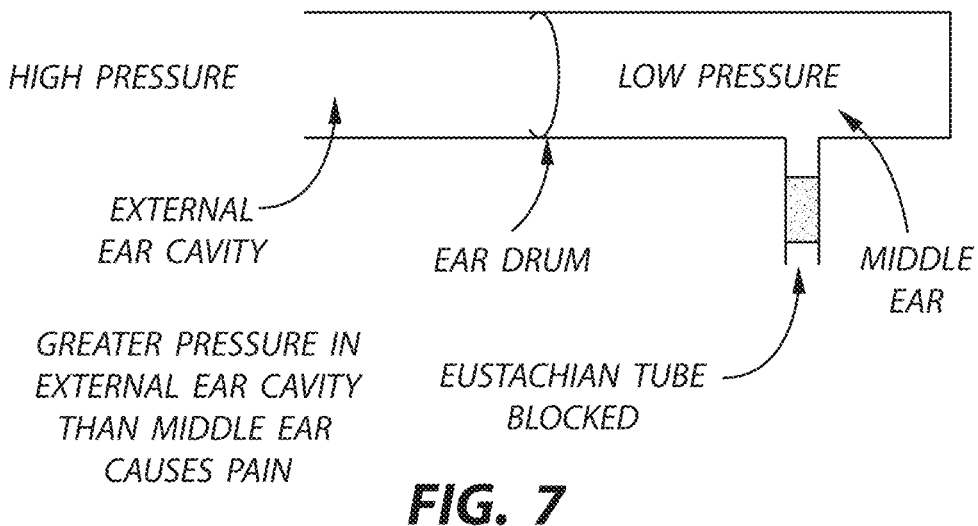
FIG. 7 is a schematic view of an ear in which there is a pressure differential between the external outside environment and the middle ear wherein the pressure in the middle ear is less than the pressure in the external environment, and wherein the Eustachian tube is blocked or not functioning normally.
Figure 8:
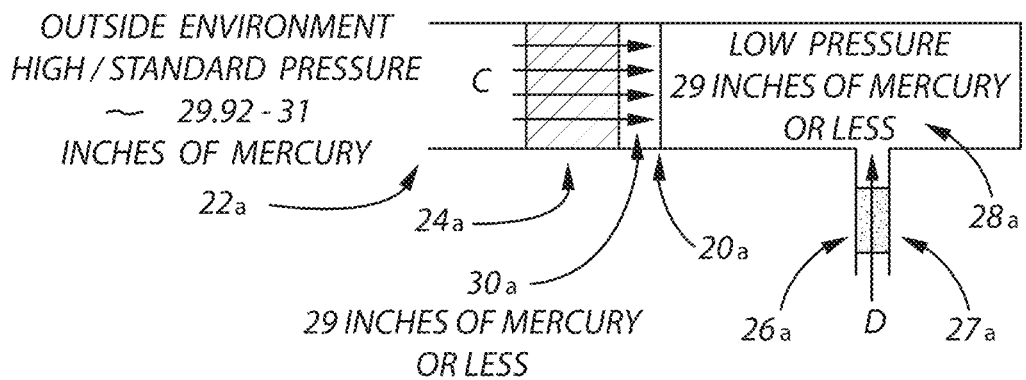
FIG. 8 is a schematic view of an ear in which an exemplary earplug configured for use with the present invention is disposed, and in which there is a pressure differential between the external outside environment and the middle ear, the pressure being less in the middle ear than in the exterior environment, illustrating a change in barometric pressure, and wherein the Eustachian tube is blocked or not functioning normally.

Similarly, FIG. 8 is a schematic illustration of the operation of the earplug configured for use with the present invention under conditions comparable to those of FIG. 7, except for the use of the exemplary embodiment of the earplug according to the present invention. More specifically, FIG. 8 depicts the effect of an increase in barometric pressure. In FIG. 8, the outside environment has a higher barometric pressure, for example 29.92 to 31 inches of mercury (14.695 to 15.225 psi; 1,013.25 to 1,049.78 mbar), than the pressure inside the middle ear 28a, which is still at the barometric pressure, for example 29 inches of mercury or lower (14.243 psi or less; 982.05 mbar or less), before the increase in barometric pressure. The pressure inside the middle ear 28a is a result of the middle ear 28a being pressurized and filled with air prior to the increase in barometric pressure, and not being able to equilibrate to the current ambient barometric pressure of the outside environment because the Eustachian tube 26a is blocked, schematically depicted by blockage 27a, so that the middle ear 28a cannot draw in air through the Eustachian tube 26a, or at least not at the desired rate sufficient to cause the desired pressurization of the middle ear 28a. However, because of the installation of the earplug 24a, which is schematically depicted in FIG. 8, the pressure in the volume 30a between the ear drum 20a and the earplug 24a remains at the prior barometric pressure before the increase in barometric pressure, and this prior barometric pressure is the same as the pressure in the middle ear 28a or at a sufficiently close pressure so as to not cause noticeable ear discomfort or barotrauma. The earplug 24a is adapted to slowly permit the inflow of air into the volume 30a through the external ear canal 22a and as shown, airflow in direction C illustrated by the arrows occurs. Similarly, provided that there is only partial blockage of the Eustachian tube 26a, airflow through the blockage 27a travels in the direction depicted by arrow D, so that the pressure in the middle ear 28a equilibrates with the current ambient pressure as it exists in the outside environment.

An exemplary embodiment of the earplug configured for use with the present invention is illustrated in FIGS. 10 and 11. FIG. 11 shows an enlarged cross-sectional view of the exemplary embodiment of the earplug 10 with each of the components identified. The earplug 10 has a body 12 shaped generally like a conventional sound attenuating ear plug body comprising a ribbed neck section 13 of the earplug 10. The ribbed neck section 13 provides an air tight seal with the walls of the ear canal when the earplug 10 is in use. The seal is important to ensure that the pressure regulation is controlled by the pressure regulator 14 and is not affected by a poorly sealed ear plug. There is a bore 15 extending through the earplug 10 to permit airflow regulated by the pressure regulator 14 therethrough. The pressure regulator 14, which is preferably made of porous metal or porous ceramic, and most preferably, porous ceramic material, permits air leakage therethrough, preferably in the range of $6.1 \times 10^{-5}$ to $1.4 \times 10^{-3}$ cc/sec. FIG. 10 shows a perspective view of the exemplary embodiment of the earplug 10 configured for use with the present invention with the plurality of ribs 17 providing a secure and leakage resistant means of retaining the earplug in the ear and preventing any air leakage except through the pressure regulator 14.

The pressure regulator 14 may be made from a porous ceramic material, and the porous ceramic material may preferably be comprised of 73.9% by weight of $Al_2O_3$, 24.6% by weight of $SiO_2$, 0.1% by weight of CaO, 0.1% by weight of MgO, 0.4% by weight of $Fe_2O_3$, 0.4% by weight of $TiO_2$, 0.3% by weight of $K_2O$ and 0.2% by weight of $Na_2O$. The porous ceramic material may also preferably be P-3-C CoorsTek material available from CoorsTek, Inc. of Golden, Colorado. The pressure regulator 14 may be made by combining the porous ceramic material with a bonding agent and forming the combination into a small right circular cylinder approximately 0.125 inches (3.18 mm) long with a diameter of 0.083 inches (2.1 mm). Once the cylinder is formed it is heated until the material fuses together and forms the solid pressure regulator 14. The porosity of the ceramic is controlled by adjusting the particle size, bonding agent, and controlling the curing temperature or the heating profile. The pressure regulator 14 may then be forced into the bore 15 of the earplug 10 which has an inside diameter of 0.078 inches (1.98 mm). The interference fit provides an air-tight seal between the pressure regulator 14 ceramic and the bore 15 of the earplug 10.

The body 12 of the earplug 10 may be made from any suitable material used for the manufacture and/or construction of earplugs. Preferably, the material used to construct the body 12 should be sufficiently air-tight so that air only passes through the pressure regulator 14, and should also be sufficiently resilient so as to be capable of forming at least a substantially air-tight seal with a user's ear canal. Even more preferably, the material may be a soft molded silicone having a durometer of between about 60 to 64 on the OO scale. It is understood that the OO scale has a spherical radius of 1.20 mm, a diameter of 2.40 mm, an extension of 2.54 mm and a spring force of 113 gf (1.11N).

An exemplary method of using the earplug 10 for the elimination or reduction of discomfort and/or barotrauma associated with barometric pressure changes, will be discussed with reference to FIGS. 4-6, 10 and 11. The user of the earplugs 10 may be aware of impending conditions that may result in the onset discomfort and/or barotrauma, such as a change in barometric pressure, and the earplug 10 may be inserted into the user's ear canals to reduce the likelihood of experiencing such symptoms. For example, the user may utilize a pressure monitoring application according to exemplary embodiments of the present invention discussed above to receive and/or obtain data related to changes in barometric pressure, including indications as to when to insert or remove the earplugs 10 as discussed above.

Figure 6:
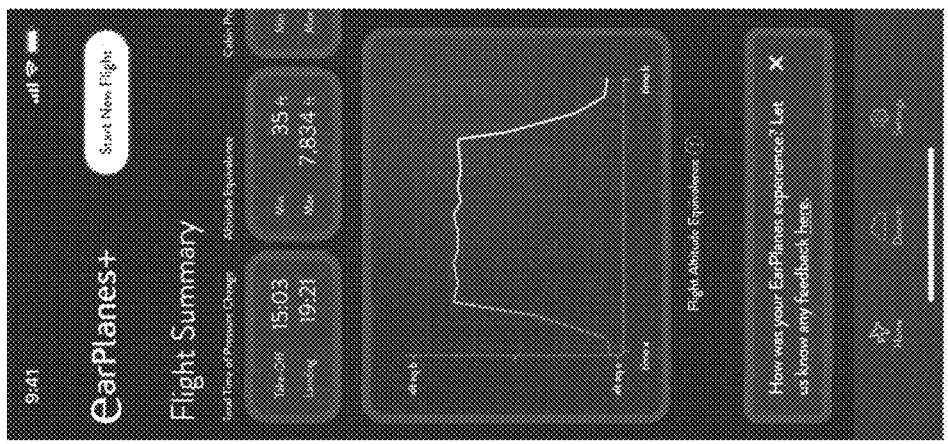
FIG. 6 shows features of the exemplary pressure monitoring application of FIG. 4.
Figure 5:
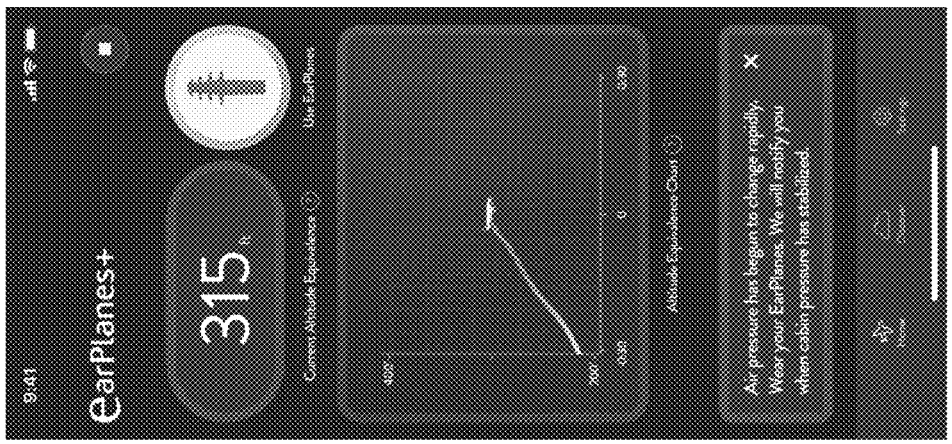
FIG. 5 shows features of the exemplary pressure monitoring application of FIG. 4.
Figure 4:
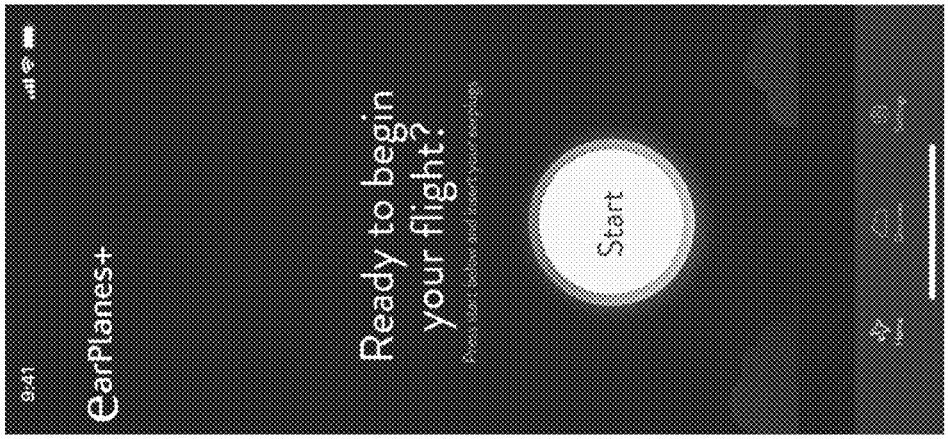
FIG. 4 shows features of an exemplary pressure monitoring application according to aspects of the present invention.

Features of an exemplary pressure monitoring application according to an exemplary embodiment of the present invention are shown in FIGS. 4-6. An exemplary screen for the initiation of the pressure monitoring application is shown in FIG. 4, and can be used to begin monitoring and logging of the ambient barometric pressure by the pressure monitoring application. For example, the initiation of the pressure monitoring application shown in FIG. 4 may correspond with the beginning of a commercial aircraft flight, either at take-off or departure from the gate. The user may begin monitoring of the ambient barometric pressure by the pressure monitoring application by selecting the "Start" icon as shown on the exemplary screen in FIG. 4.

As shown by the exemplary barometric charts in FIGS. 5 and 6 generated by the pressure monitoring application, the barometric pressure readings may be organized for presentation on the user device as a chart of the barometric pressure at predetermined intervals during the selected time frame. The chart may include an indication of when to insert the earplugs 10 or keep the earplugs 10 inserted, for example by displaying a graphic of an earplug within the screen of the pressure monitoring application as in FIG. 5. Likewise, the pressure monitoring application may display an indication or remove an indication from the screen when the earplugs 10 are no longer required as a result of the ambient barometric pressure stabilizing or reaching other threshold criteria. As shown in FIG. 6, the pressure monitoring application may be provided to display a summary of the monitored pressures over the entire duration of monitoring, for example for the entire flight. This information can be saved in the pressure monitoring application and retrieved for future use, for example if the user will be traveling along the same route or other similar travel itinerary.

An exemplary use of the pressure monitoring application will now be discussed with reference to exemplary barometric pressures and thresholds for initiating protective measures, such as earplugs having pressure regulators therein. The user of the pressure monitoring application initiates pressure monitoring (FIG. 1B—step 169) by the pressure monitoring application. In this example, the user has set the predetermined intervals for determining the ambient barometric pressure at the user's electronic device, e.g., "smart" phone, containing the pressure monitoring application at one second. Accordingly, at time $T_1$ the pressure monitoring application determines the ambient barometric pressure, for example by receiving a reading of the ambient barometric pressure from a barometer within and/or coupled to the electronic device. One predetermined interval later, in this example one second, at time $T_2$ the pressure monitoring application determines the ambient barometric pressure again (FIG. 1B—step 172). The pressure monitoring application is then configured to determine the pressure change over the predetermined interval by taking the absolute value of the ambient barometric pressure at time $T_1$ minus the ambient barometric pressure at time $T_2$ divided by the duration of the predetermined interval. For example, if the ambient barometric pressure at time $T_1$ was 1000 mbar, and the ambient barometric pressure at time $T_2$ was 995 mbar the pressure change would be 5 mbar/sec. The pressure monitoring application then compares this pressure change with a predetermined or preset threshold to determine whether the pressure monitoring application should provide an indication to the user to employ protective measures (FIG. 1C—step 178). The threshold may be correlated to the magnitude of pressure change either over the predetermined interval, another period of time or both that is likely to cause ear discomfort and/or barotrauma. For example, a pressure change of approximately 20 mbar may result in the Eustachian tube opening and causing a popping sensation for the user's ears. While this alone may not cause ear discomfort and/or barotrauma, this pressure change of 20 mbar may be sufficient to cause ear discomfort and/or barotrauma in the event the Eustachian tube is blocked and/or does not open as normal. Accordingly, in this example, the threshold may be set at 20 mbar/sec or at a lower rate of pressure change, such as 3 mbar/sec in order to allow the user some opportunity to initiate the protective measures prior to a total pressure change that may result in ear discomfort and/or barotrauma. In other words, the pressure monitoring application may be configured to identify an immediate pressure change likely to result in ear discomfort and/or barotrauma and to predict a cumulative pressure change likely to result in ear discomfort and/or barotrauma. For example, using the pressure change of 5 mbar/sec from the above example, would result in a predicted cumulative pressure change of 300 mbar/min if pressure change was constant. It is understood that any values for the measured ambient barometric pressure, threshold and/or pressure change are merely exemplary and the present invention is not limited to any particular values. Instead, the values are merely provided to facilitate a better understanding of the functionality and advantages of the present invention.

Unless the user has discontinued pressure monitoring by the pressure monitoring application (FIG. 1C—step 186), the pressure monitoring application will continue to determine the ambient barometric pressure at the predetermined intervals. For example, at time $T_3$, which in the example above would be one second after $T_2$ and two seconds after $T_1$, the pressure monitoring application may determine the barometric pressure to be 1001 mbar. As a result, the pressure change of $T_2$ relative to $T_3$ would be 6 mbar/sec, and if this pressure change is over the set threshold the indication to employ protective measures would be provided (FIG. 1C—step 178) or a previous indication would still apply. As evident from this example, the pressure change from $T_1$ to $T_3$ would be 1 mbar/sec, which may be lower than the set threshold of 3 mbar/sec, but by determining the pressure change for each predetermined interval the pressure monitoring application can also address ambient barometric pressure variability which may also cause ear discomfort and/or barotrauma. As an alternative, the pressure monitoring application may be configured to take the average of ambient barometric pressures over a number of predetermined intervals and compare this average to an ambient barometric pressure taken at a set time or an average of barometric pressures taken over other predetermined intervals, for example a rolling average. However, if the ambient barometric pressure taken at time $T_3$ was 994 mbar, the pressure change between $T_2$ and $T_3$ would be 1 mbar/sec, and potentially below the set threshold. Accordingly, the pressure monitoring application would be configured to provide an indication to the user to discontinue the protective measures (FIG. 1C—step 184). If the user has not discontinued pressure monitoring (FIG. 1C—step 186) by the pressure monitoring application, the pressure monitoring application will continue to determine the ambient barometric pressure at the next predetermined interval, which in the example provided would be time $T_4$. If the threshold was 3 mbar/sec, an ambient barometric pressure taken at time $T_4$ (one second after time $T_3$) of less than 991 mbar or greater than 997 mbar (when ambient barometric pressure at time $T_3$ is 994 mbar) would result in provision of an indication to the user to employ, or maintain, protective measures (FIG. 1C—step 178). However, if the ambient barometric pressure taken at time T4 was between 991 and 997 mbar, resulting in a pressure change is less than 3 mbar/sec, the pressure monitoring application would be configured to provide an indication to the user to discontinue the protective measures (FIG. 1C—step 184).

In order to reduce the amount of times a user must employ and then discontinue the protective measures, the pressure monitoring application may be configured so as to require a certain number of consecutive pressure changes over a number of predetermined intervals to be below the threshold. For example, the pressure monitoring application may be configured to require ten consecutive pressure changes over ten predetermined intervals to be below the threshold before providing an indication to the user to discontinue the protective measures. In this manner, this may reduce the likelihood the user experiences ear discomfort and/or barotrauma as a result of inopportune and/or untimely employment or discontinuance of the protective measures. Another alternative, may be for the pressure monitoring application to compare pressure changes from non-sequential predetermined intervals so that the pressure change over a sufficiently large period of time is determined for whether to provide an indication to discontinue the protective measures.

It will thus be seen that the objects set forth above, among those made apparent from the preceding description, are efficiently attained and, since certain changes may be made in the above article without departing from the scope of this invention, it is intended that all matter contained in this disclosure or shown in the accompanying drawings, shall be interpreted, as illustrative and not in a limiting sense. It is to be understood that all of the present figures, and the accompanying narrative discussions of corresponding embodiments, do not purport to be completely rigorous treatments of the invention under consideration. It is to be understood that the above-described arrangements are only illustrative of the application of the principles of the present invention. Numerous modifications and alternative arrangements may be devised by those skilled in the art without departing from the scope of the present invention.

What is claimed is:

1. A method for monitoring air pressure change, comprising:
   receiving a user input selecting a pressure monitoring application,
   receiving a user input initiating monitoring of an ambient air pressure by the pressure monitoring application,
   determining a first barometric pressure of the ambient air pressure at a first time,
   determining a second barometric pressure of the ambient air pressure at a second time, wherein the second time is a predetermined time interval from the first time,
   comparing the first barometric pressure with the second barometric pressure to determine a first absolute rate of change of the ambient air pressure over the predetermined time interval, and
   providing an indication to employ protective measures when the first absolute rate of change of the ambient air pressure is equal to or a exceeds a threshold rate of change likely to cause barotrauma.

2. The method according to claim 1, further comprising determining a third barometric pressure of the ambient air pressure at a third time, wherein the third time is the predetermined time interval from the second time,
   comparing the second barometric pressure with the third barometric pressure to determine a second absolute rate of change of the ambient air pressure over the predetermined time interval,
   continuing to provide the indication to employ protective measures when the second absolute rate of change of the ambient air pressure over the predetermined time interval is equal to or exceeds the threshold rate of change likely to cause barotrauma, and
   providing an indication to discontinue protective measures when the second absolute rate of change of the ambient air pressure over the predetermined time interval is less than the threshold rate of change likely to cause barotrauma.

3. The method according to claim 2, wherein at least the first barometric pressure, the second barometric pressure and the third barometric pressure are organized for presentation as a graph of measured ambient air pressure over time.

4. The method according to claim 1, wherein the protective measures comprise a pair of earplugs each having a pressure regulator with an air leakage rate of $6.1 \times 10^{-5}$ to $1.4 \times 10^{-3}$ cc/sec, and wherein employing the protective measures comprises inserting the earplugs into ear canals of a user.

5. The method according to claim 1, wherein the threshold rate of change is at least 3 mbar/sec.

6. The method according to claim 1, further comprising determining a fourth barometric pressure of the ambient air pressure at a fourth time, wherein the fourth time is the predetermined time interval from the third time, and comparing the third barometric pressure with the fourth barometric pressure to determine a third absolute rate of change of the ambient air pressure over the predetermined time interval.

7. The method according to claim 1, further comprising storing at least the first barometric pressure and the second barometric pressure for retrieval at a later time.

8. An apparatus comprising at least one processor and at least one memory including an application that is executable by the at least one processor to cause the apparatus at least to carry out a method for monitoring air pressure change, comprising:
receiving a user input selecting a pressure monitoring application,
receiving a user input initiating monitoring of an ambient air pressure by the pressure monitoring application,
determining a first barometric pressure of the ambient air pressure at a first time,
determining a second barometric pressure of the ambient air pressure at a second time, wherein the second time is a predetermined time interval from the first time,
comparing the first barometric pressure with the second barometric pressure to determine a first absolute rate of change of the ambient air pressure over the predetermined time interval, and
providing an indication to employ protective measures when the first absolute rate of change of the ambient air pressure is equal to or a exceeds a threshold rate of change likely to cause barotrauma.

9. The apparatus according to claim 8, wherein the application is executable by the at least one process to further cause the apparatus to carry out determining a third barometric pressure of the ambient air pressure at a third time, wherein the third time is the predetermined time interval from the second time,
comparing the second barometric pressure with the third barometric pressure to determine a second absolute rate of change of the ambient air pressure over the predetermined time interval,
continuing to provide the indication to employ protective measures when the second absolute rate of change of the ambient air pressure over the predetermined time interval is equal to or exceeds the threshold rate of change likely to cause barotrauma, and
providing an indication to discontinue protective measures when the second absolute rate of change of the ambient air pressure over the predetermined time interval is less than the threshold rate of change likely to cause barotrauma.

10. The apparatus according to claim 9, wherein at least the first barometric pressure, the second barometric pressure and the third barometric pressure are organized for presentation as a graph of measured ambient air pressure over time.

11. The apparatus according to claim 8, wherein the protective measures comprise a pair of earplugs each having a pressure regulator with an air leakage rate of $6.1 \times 10^{-5}$ to $1.4 \times 10^{-3}$ cc/sec, and wherein employing the protective measures comprises inserting the earplugs into ear canals of a user.

12. The apparatus according to claim 8, wherein the threshold rate of change is at least 3 mbar/sec.

13. The apparatus according to claim 8, wherein the application is executable by the at least one process to further cause the apparatus to carry out determining a fourth barometric pressure of the ambient air pressure at a fourth time, wherein the fourth time is the predetermined time interval from the third time, and comparing the third barometric pressure with the fourth barometric pressure to determine a third absolute rate of change of the ambient air pressure over the predetermined time interval.

14. The apparatus according to claim 8, wherein the application is executable by the at least one process to further cause the apparatus to carry out storing at least the first barometric pressure and the second barometric pressure for retrieval at a later time.

15. A nontransitory computer readable medium having a computer program stored thereon that is executable by a processor for causing a portable electronic display device to carry out the method for monitoring air pressure change, comprising:
receiving a user input selecting a pressure monitoring application,
receiving a user input initiating monitoring of an ambient air pressure by the pressure monitoring application,
determining a first barometric pressure of the ambient air pressure at a first time,
determining a second barometric pressure of the ambient air pressure at a second time, wherein the second time is a predetermined time interval from the first time,
comparing the first barometric pressure with the second barometric pressure to determine a first absolute rate of change of the ambient air pressure over the predetermined time interval, and
providing an indication to employ protective measures when the first absolute rate of change of the ambient air pressure is equal to or a exceeds a threshold rate of change likely to cause barotrauma.

16. The nontransitory computer readable medium having the computer program stored thereon according to claim 15, that is executable by the processor for causing the portable electronic display device to further carry out determining a third barometric pressure of the ambient air pressure at a third time, wherein the third time is the predetermined time interval from the second time,
comparing the second barometric pressure with the third barometric pressure to determine a second absolute rate of change of the ambient air pressure over the predetermined time interval,
continuing to provide the indication to employ protective measures when the second absolute rate of change of the ambient air pressure over the predetermined time interval is equal to or exceeds the threshold rate of change likely to cause barotrauma, and
providing an indication to discontinue protective measures when the second absolute rate of change of the ambient air pressure over the predetermined time interval is less than the threshold rate of change likely to cause barotrauma.

17. The nontransitory computer readable medium having the computer program stored thereon according to claim 15, wherein the protective measures comprise a pair of earplugs each having a pressure regulator with an air leakage rate of $6.1 \times 10^{-5}$ to $1.4 \times 10^{-3}$ cc/sec, and wherein employing the protective measures comprises inserting the earplugs into ear canals of a user.

18. The nontransitory computer readable medium having the computer program stored thereon according to claim 15, wherein the threshold rate of change is at least 3 mbar/sec.

19. The nontransitory computer readable medium having the computer program stored thereon according to claim 15, that is executable by the processor for causing the portable electronic display device to further carry out determining a fourth barometric pressure of the ambient air pressure at a fourth time, wherein the fourth time is the predetermined time interval from the third time, and
comparing the third barometric pressure with the fourth barometric pressure to determine a third absolute rate of change of the ambient air pressure over the predetermined time interval.

20. The nontransitory computer readable medium having the computer program stored thereon according to claim 15, wherein at least the first barometric pressure, the second barometric pressure and the third barometric pressure are organized for presentation as a graph of measured ambient air pressure over time.

* * * * *